RADIOIMMUNOASSAY OF ANGIOTENSIN AND RENIN ACTIVITY

Original Filed Jan. 19, 1968

INVENTOR.
ROBERT L. WOLF
BY Brumbaugh, Free, Graves & Donohue
his ATTORNEYS.

United States Patent

Re. 28,442
Reissued June 3, 1975

28,442
RADIOIMMUNOASSAY OF ANGIOTENSIN AND RENIN ACTIVITY

Robert L. Wolf, New York, N.Y., assignor to Mount Sinai School of Medicine of the City University of New York, New York, N.Y.

Original No. 3,592,888, dated July 13, 1971, Ser. No. 699,098, Jan. 19, 1968. Application for reissue Sept. 7, 1972, Ser. No. 286,983
Int. Cl. A61k *27/04;* G01n *23/00*
U.S. Cl. 424—1 10 Claims

Matter enclosed in heavy brackets [ ] appears in the original patent but forms no part of this reissue specification; matter printed in italics indicates the additions made by reissue.

ABSTRACT OF THE DISCLOSURE

A process for assaying the quantity of angiotensin and renin employing radioimmunoassay techniques, comprising the steps of combining solutions of (1) antibody to angiotensin coupled to poly-L-lysine, (2) angiotensin labeled with radioactivity, and (3) varying known amounts of unlabeled angiotensin, to produce mixtures having a pH of about 7.0 to 9.5, which upon incubation form angiotensin-antibody complexes. The mixtures of angiotensin-antibody complexes (antibody-bound angiotensin) and free angiotensin are applied either to paper strips, coated charcoal, ion exchange resins or resin sponges, and subjected to radioimmunoassay techniques to separate the antibody-bound angiotensin complexes from the free angiotensin. Some of the free and antibody-bound angiotensin is radioactive; the ratio of radioactivity of the antibody-bound angiotensin complex to free angiotensin is plotted as a function of the known concentrations of angiotensin in each mixture to prepare a standard concentration graph. The process is repeated employing unknown amounts of unlabeled angiotensin, which may be derived from the action of renin on renin substrate, and the concentration of angiotensin is read from the graph.

This invention relates to a process for detecting and measuring quantities of angiotensin and renin and, more particularly, to a process for employing the techniques of radioelectrophoresis to assay quantities of angiotensin and renin.

Angiotensin II is a physiologically active octapeptide hormone which increases the blood pressure when present in the body. Renin substrate is the precursor of angiotensin and is converted to angiotensin by the enzyme renin which is produced in the kidney. Although angiotensin alone is unable to elicit the production of a specific antibody, it is known that angiotensin can promote the production of a specific antibody in animals, when the angiotensin is coupled with a carrier molecule, poly-L-lysine, at the carboxyl-terminal phenylalanine or amino-terminal asparagine ends of angiotensin. The antibody combines with angiotensine to form an angiotensin-antibody complex.

Researchers in the field have also found that the angiotensin may be identified as it complexes with the antibody by labeling the angiotensin with a radioactive isotope, such as iodine 131 or 125. The angiotensin-$I^{131}$-antibody complex forms when the two are mixed. The angiotensin antibody complexes with equal affinity with either unlabeled or labeled angiotensin, and therefore, as unlabeled angiotensin is added to the labeled angiotensin-antibody mixtures, the amount of free angiotensin-$I^{131}$ increases.

It is therefore an object of this invention to provide a process for separating the radioactive angiotensin-antibody complexes (bound angiotensin) from free radioactive angiotensin. It is furthermore an object of this invention to provide a method for rapidly determining the concentrations or quantities of unknown amounts of angiotensin and renin.

In accordance with the invention, the objects are achieved by the following process. Mixtures are formed containing three components: (1) the antibody to angiotensin, which has been made antigenic by coupling the angiotensin to the carrier molecule poly-L-lysine by means of its carboxylterminal phenylalanine (A-(Phe)-PL) or amino-terminal asparagine (PL(Asn)-A), (2) radioactively labeled angiotensin (iodine 131, iodine 125, etc.), and (3) varying known amounts of unlabeled angiotensin. The mixtures should be in the range of approximately pH 7.0 to 9.5, and are allowed to incubate to form angiotensin-antibody complexes. The mixtures are then subjected to one of the following three radioimmunoassay techniques to separate the antibody-bound angiotensin complex from the free angiotensin: (1) paper radioelectrophoresis, (2) coated charcoal, or (3) ion exchange resins or resin-sponges.

Figure 1:
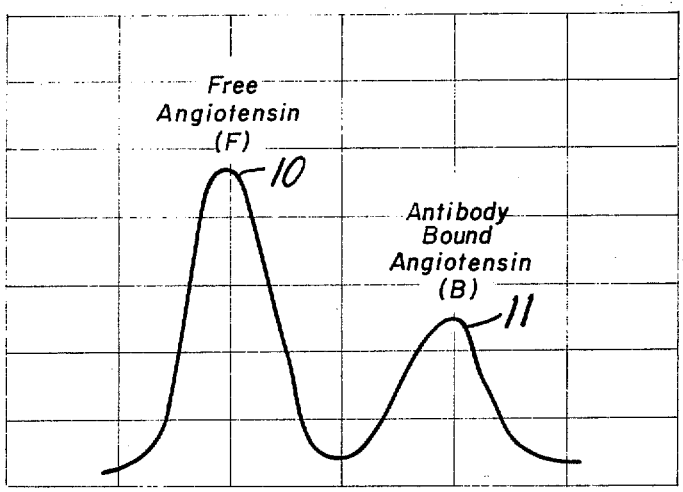
FIG. 1 is a radioelectrophoretogram showing the relationship of the radioactivities of free angiotensin-$I^{131}$ and antibody-bound angiotensin.

Following the separation of the antibody-bound angiotensin complex from the free angiotensin, the radioactivities in the complex and in the free angiotensin group are counted to prepare a radioelectrophoretogram as shown in FIG. 1, wherein the radioactivities of the antibody-bound angiotensin complex 10 and the free angiotensin-$I^{131}$ 11 are located in separate peaks permitting visual comparision and computation of the relative areas under each peak.

Figure 2:
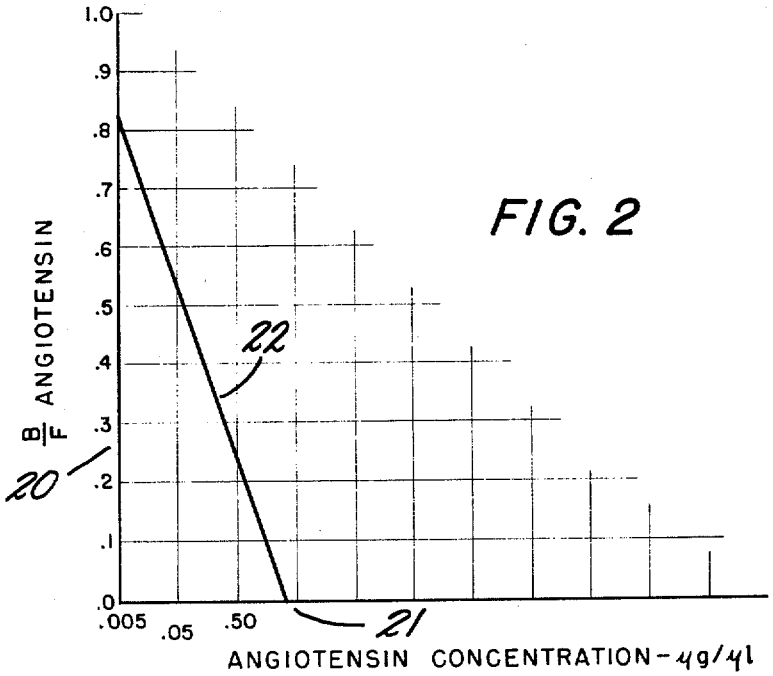
FIG. 2 represents a graph illustrating the relationship between the ratio of radioactive angiotensin-antibody complexes to free angiotensin-$I^{131}$ and the concentration of angiotensin.

A standard line graph as shown in FIG. 2 is prepared by plotting the ratio 20 of the radioactivity of the antibody-bound angiotensin complex to the radioactivity of the free angiotensin-$I^{131}$ as functions 22 of the varying known amounts of unlabeled angiotensin 21 contained in each mixture. Since the amount of labeled angiotensin present in each mixture infinitesimal in comparison with the amount of unlabeled angiotensin added, it is simpler in practice to use the total of the amounts of labeled and unlabeled angiotensin present in the mixture to plot the line graph.

The concentration of unknown amounts of angiotensin in solution is determined by substituting the unknown angiotensin solution for the known amounts of unlabeled angiotensin in the mixture described above. The process is then repeated to determine the ratio of the radioactive antibody-bound angiotensin complex to free angiotensin-$I^{131}$. The ratio is located on the line graph, from which the concentration of the unknown solution of angiotensin may be immediately established.

In formulating the mixtures of angiotensin antibody, angiotensin-$I^{131}$, and unlabeled angiotensin, it has been found advantageous to prepare the mixtures in a solution of buffer containing approximately 0.25% to 0.5% human serum albumin, and to maintain the pH between 7.0 and 9.5, perferably about 8.6. In order to establish efficiently the known quantities of angiotensin in the standard mixtures and to ensure the purity of the angiotensin samples, it is preferred to use synthetic angiotensin.

Although antibodies from any standard research animal may be used, such as dog, hamster, or guinea pig, excellent results have been obtained using rabbit antibody.

In applying the technique of paper radioelectrophoresis, it has been found that the following conditions provide excellent results. A great saving of time and effort may be achieved if several mixtures are processed simultaneously. Mixtures containing varying known amounts of synthetic angiotensin may be processed at the same time that mixture containing unknown amounts of angiotensin are being processed.

The mixtures are refrigerated at approximately 4° C. for approximately twenty-four hours. During this period of time, both the labeled and unlabeled angiotensin combine with the antibody to form angiotensin-antibody complexes. Portions of the mixture are applied to the cathode ends of strips of Whatman No. 3MM filter paper. The filter paper is placed on horizontal supports with the two ends immersed in buffer solutions, and a potential of approximately 200 volts is applied across the paper for 10 to 25 hours. The buffer solution employed has a pH of approximately 8.6 with an ionic strength of approximately 0.1. Satisfactory separation of the angiotensin-antibody complex from free angiotensin is accomplished under these conditions.

If desired, a quantity of nonimmune (control) rabbit plasma or serum may be added to each mixture tube to prevent adsorption to the paper or glass of antigen-antibody complexes which are present in low concentrations. The paper strips are then dried and assayed for radioactivity in an automatic strip scanner employing a linear ratemeter with an integrating count circuit. The protein in the strips may be stained with naphthalene black and 10% acetic acid in methyl alcohol.

It has been observed that the angiotensin-antibody complex migrates with the mobility of gamma globulin in the anodal direction. The free angiotensin, however, migrates more rapidly in the anodal direction, which results in the desired separation of the two groups.

The ratio of bound to free radioactive angiotensin is plotted on a graph as a function of the varying known concentrations of unlabeled angiotensin contained in the mixtures. It is preferred to dilute the mixture appropriately to yield an initial bound to free ratio of between 1.5 and 3.0 in the absence of added unlabeled angiotensin. It is also desirable to select an antiserum (rabbit antibody to angiotensin coupled to poly-L-lysine) which will result in a sharp slope of decline of the ratio of bound to free radioactive angiotensin with increasing angiotensin concentration. The resulting graph may be used to find the concentration of unlabeled angiotensin in .001 (mμ g.) quantities.

The mixtures containing unknown amounts of unlabeled angiotensin are subjected to the same paper radioelectrophoresis technique as discussed above. The ratio of bound radioactive angiotensin to free radioactive angiotensin is then located on the standard line graph prepared as described above. From the graph the concentration of the unknown amounts of angiotensin may immediately be determined.

As an alternative method of separating the radioactive antibody-bound angiotensin complexes from the free angiotensin-$I^{131}$, a procedure may be employed utilizing coated charcoal. According to this procedure, portions of the mixtures containing the known and unknown angiotensin specimens are applied to solutions of charcoal powder coated with dextran. The charcoal is precipitated by centrifugation and contains the free angiotensin. The supernatant fluid contains the radioactive antibody-bound angiotensin complexes, and the radioactivity is counted in a well-type scintillation counter.

The ratio of the radioactive antibody-bound angiotensin complex to free angiotensin-$I^{131}$ is plotted as a function of the angiotensin concentration, as described above in connection with the paper radioelectrophoresis technique. The angiotensin concentration in the mixtures may be readily determined by the use of the standard line graph.

Another method of separating the antibody-bound angiotensin complexes from the free angiotensin-$I^{131}$ employs the use of ion exchange resins or resin-sponges. According to this technique, portions of the mixtures containing the standard and unknown angiotensin specimens are applied to ion exchange resins or resin-sponges. The effluent or supernatant fluid retains the antibody-bound angiotensin complexes while the free angiotensin-$I^{131}$ is adsorbed onto the ion exchange resin or resin-sponge. The supernatant fluid and the resins are then processed to count the radioactivity in a manner similar to the techniques outlined above for coated charcoal. A standard graph is prepared for use in determining the concentration of angiotensin contained in the unknown angotensin specimens.

The process of the invention may also be used to determine the activity of renin. In order to assay the activity of renin, the fluid containing the renin is immediately cooled to about 0° C. to 5° C. An anticoagulant may be added, such as the ammonium salt of ethylenediaminetetraacetic acid. The renin-containing fluid (plasma) is incubated at a pH of about 5.5 and at a temperature of about 37° C. with an ammonium type resin (such as Dowex resin 50 W–X2). The resulting angiotensin, which is liberated during incubation, is adsorbed onto the resin and protected from inactivation by the angiotensinases. The adsorbed angiotensin is then eluted from the resin and assayed as described above according to one of the three radioimmunoassay techniques.

The following example is intended to be illustrative of the process of the invention, and is not to be considered as defining the scope of the invention.

EXAMPLE

Two standard mixtures of (1) rabbit antiserum to angiotensin, (2) labeled synthetic angiotensin-$I^{131}$, and (3) unlabeled synthetic angiotensin were prepared having angiotensin concentrations of 0.005 μg./30 μl. and 0.05 μg./30 μl. A third mixture of (1) antiserum (antibody), (2) labeled synthetic angiotensin, and (3) unlabeled angiotensin in an unknown concentration was also prepared. The three mixtures were prepared in buffer solutions at pH 8.6 containing 0.25% human serum albumin and incubated at 4° C. for 24 hours. 50 μl. of nonimmune (control) rabbit plasma were added to each mixture to prevent adsorption onto the paper during radioelectrophoresis. Portions of the three mixtures were applied to strips of Whatman No. 3MM filter paper, and the ends of the strips were placed in barbital buffer solutions at pH 8.6 and an ionic strength of 0.1. Radioelectrophoresis was effected at a constant temperature of 4° C. for 18 hours with a 200 volt potential. The strips were assayed for radioactivity after drying, employing an automatic strip scanner connected to a linear ratemeter with an integrating count circuit and a dual channel recorder. The areas under the two peaks of the paper radioelectrophoretogram representing the radioactivity of the free angiotensin-$I^{131}$ and the radioactivity of the labeled angiotensin-antibody complex were determined, and the ratios of bound to free angiotensin-$I^{131}$ were ascertained. The ratios were 0.83 and 0.53 for the known solutions and 0.24 for the unknown solution. The first two ratios were plotted on graph paper as functions of the known concentrations of unlabeled angiotensin to produce two points. The points were connected with a straight line to form a line graph. The ratio of the unknown solution was located on the line graph and the concentration of the unknown solution of angiotensin was found to be 0.5 μg./30 μl.

The process described herein may thus be used to assay the activity of angiotensin and of renin in an efficient and rapid manner. The concentration of a sample of angiotensin is readily determined with the use of the standard graphs, thereby providing the solution to a problem long recognized in the art.

I claim:

1. A process for assaying angiotensin activity comprising the following steps: (1) preparing an amount of antibody to angiotensin coupled to poly-L-lysine; (2) labeling an amount of angiotensin with radioactivity; (3)

preparing solutions containing varying known amounts of unlabeling angiotensin, a [quatity] *quantity* of the antibody and a quantity of labeled angiotensin in order to form mixtures having a pH of about 7.0 to 9.5 containing radioactive antibody-bound angiotensin complexes and antibody-bound unlabeled angiotensin complexes; (*4*) subjecting said mixtures to paper radioelectrophoresis to separate the antibody-bound angiotensin complexes from the free angiotensin on paper strips; (*5*) counting the radioactivity in both bound and free angiotensin groups on the paper strips to determine the ratios of the radioactive antibody-bound angiotensin complexes to the radioactive free angiotensin; (*6*) [plotting on a graph] *referencing* the ratios of bound to free radioactive angiotensin [as a function of] *to* the known amounts of angiotensin in [each of the] *said* mixtures to establish a [line graph showing the] relationship between the ratio of bound to free angiotensin and the concentration of angiotensin; (*7*) repeating [the process recited] *steps* (*1*) *to* (*5*), *inclusive,* above using an unknown amount of unlabeled angiotensin in [said] *a* mixture to determine the ratio of bound labeled angiotensin to free labeled angiotensin *in said mixture;* and (*8*) [locating the ratio on the line graph] *using the relationship previously established according to step* (*6*) to determine the concentration of the unknown amount of angiotensin.

[2. A process as set forth in claim 1, wherein said mixtures of bound and free angiotensin are applied to a dispersion of charcoal powder coated with dextran, precipitating the charcoal leaving a supernatant liquid, measuring the radioactivities in the supernatant liquid and the coated charcoal, and plotting on a graph the ratio of the radioactivity of the antibody-bound angiotensin complex contained in the supernatant fluid to the radioactivity of the free angiotensin contained on the charcoal in the manner set forth in claim 1.]

[3. A process as set forth in claim 1, wherein the mixtures of bound and free angiotensin are applied to ion exchange resins or resin-sponges to yield an eluate or a supernatant liquid, measuring the radioactivity in the supernatant liquid and in the resins, and plotting on a graph the ratio of the radioactivity of antibody-bound angiotensin complex contained in the supernatant fluid to the radioactivity of the free angiotensin contained in the resins in the manner set forth in claim 1.]

4. A process as set forth in claim 1, wherein said paper radioelectrophoresis is effected by applying aliquots of the mixtures of bound and free angiotensin to the cathode ends of strips of filter paper, the ends of the paper strips are immersed in buffer solutions at approximately pH 8.6 and approximately 0.1 ionic strength, and a potential of approximately 200 volts is applied across said strips for 10 to 25 hours to separate the antibody-bound angiotensin complexes from the free angiotensin.

5. A process as set forth in claim 1, wherein the mixtures of (1) antibody, (2) labeled angiotensin, and (3) unlabeled angiotensin are prepared in a buffer solution, containing 0.25% to 0.5% human serum albumin.

6. A process as set forth in claim 1, wherein nonimmune plasma is added to the mixture of bound and free angiotensin to prevent adsorption of the angiotensin-antibody complexes to the strip paper.

7. A process as set forth in claim 1, wherein the mixtures of antibody and radioactive angiotensin are diluted to yield an initial bound to free radioactive angiotensin ratio of from approximately 1.5 to 3.0 in the absence of added unlabeled angiotensin.

8. A process as set forth in claim 1, wherein the protein on the paper strips is stained with naphthalene black and 10% acetic acid in methyl alcohol.

9. A process as set forth in claim 1, wherein the antibody to angiotensin is produced by rabbits.

10. A process for assaying renin activity comprising the following steps: cooling the fluid containing renin to between 0° C. and 5° C.; adding a blood anticoagulant to the renin-containing fluid; incubating the renin-containing fluid on an ammonium type resin at approximately pH 5.5 at approximately 37° C. to liberate angiotensin; adsorbing the liberated angiotensin onto the resin; eluting the angiotensin from the resin, and assaying the angiotensin according to the process set forth in claim 1.

*11. A process set forth in claim 1, wherein the relationship between the ratio of bound to free angiotensin and the concentration of angiotensin is determined according to step (6) by plotting on a graph the ratios of bound to free radioactive angiotensin as a function of the known amounts of angiotensin in said mixtures to provide a line graph representation of said relationship, and the concentration of the unknown amount of angiotensin is determined according to step (8) by locating the ratio determined according to step (7) on said line graph.*

*12. A process for assaying angiotensin activity comprising the following steps: (1) preparing an amount of antibody to angiotensin coupled to poly-L-lysine, (2) labeling an amount of angiotensin with radioactivity, (3) preparing solutions containing varying known amounts of unlabeled angiotensin, a quantity of antibody and a quantity of labeled angiotensin in order to form mixtures having a pH of about 7.0 to 9.5 containing radioactive antibody-bound angiotensin complexes and antibody-bound unlabeled angiotensin complexes; (4) applying said mixtures to ion exchange resins or resin-sponges to yield an eluate or a supernatant liquid; (5) measuring the radioactivities in the supernatant liquid and in the resins; (6) determining the ratio of the radioactivity of the antibody-bound angiotensin complex contained in the supernatant liquid to the radioactivity of the free angiotensin in the resins as a function of the known amounts of angiotensin in said mixtures to establish a relationship between the ratio of bound to free angiotensin and the concentration of angiotensin; (7) repeating steps (1) to (5), inclusive, using an unknown amount of unlabeled angiotensin in a mixture to determine the ratio of bound, labeled angiotensin to free, labeled angiotensin; and (8) using the relationship previously determined according to step (6) to determine the concentration of the unknown amount of angiotensin.*

References Cited

The following references, cited by the Examiner, are of records in the patented file of this patent or the original patent.

UNITED STATES PATENTS

| | | | |
|---|---|---|---|
| 3,261,747 | 7/1966 | Commerford | 424—1 |
| 3,321,463 | 5/1967 | Moffatt | 424—1 |
| 3,555,143 | 1/1971 | Axen et al. | 424—1 |

OTHER REFERENCES

Bayly: "Nucleonics." vol. 24, No. 6, June 1966, pp. 46–53.

BENJAMIN R. PADGETT, Primary Examiner

U.S. Cl. X.R.

23—230 B